United States Patent [19]

Hässlin et al.

[11] Patent Number: 4,938,797
[45] Date of Patent: Jul. 3, 1990

[54] PROCESS FOR THE PREPARATION OF MICROCAPSULES

[75] Inventors: Hans W. Hässlin, Grenzach-Wyhlen, Fed. Rep. of Germany; Michael J. Hopkinson, Pleasant Garden, N.C.

[73] Assignee: Ciba-Geigy Corporation, Ardsley, N.Y.

[21] Appl. No.: 203,791

[22] Filed: Jun. 7, 1988

Related U.S. Application Data

[63] Continuation of Ser. No. 73,324, Jul. 13, 1987, abandoned, which is a continuation of Ser. No. 776,080, Sep. 13, 1985, abandoned.

[51] Int. Cl.$^5$ .................... A01N 37/18; A61K 31/675
[52] U.S. Cl. ........................................ 71/118; 514/86; 514/93; 514/122; 514/134; 514/147; 514/144; 514/148; 514/256; 514/365; 514/383; 514/469; 514/473; 514/352; 514/513; 514/726; 514/433; 514/625; 514/755; 514/431; 514/637; 514/646; 71/88; 71/92; 71/93; 71/94; 71/98; 71/114; 71/100; 71/120; 71/121; 71/124; 71/126; 71/DIG. 1
[58] Field of Search ........................... 71/DIG. 1, 118; 514/383, 86, 93, 122, 134, 147, 469, 365

[56] References Cited

U.S. PATENT DOCUMENTS

| | | | |
|---|---|---|---|
| 4,230,809 | 10/1980 | Heinrich et al. | 424/16 |
| 4,280,833 | 7/1981 | Beestman et al. | 71/100 |
| 4,285,720 | 8/1981 | Scher | 264/4.7 |
| 4,303,548 | 12/1981 | Shimazaki et al. | 264/4.7 |
| 4,417,916 | 11/1983 | Beestman et al. | 71/93 |
| 4,563,212 | 1/1986 | Becher et al. | 71/DIG. 1 |

*Primary Examiner*—Richard L. Raymond
*Assistant Examiner*—Mark W. Russell
*Attorney, Agent, or Firm*—Edward McC. Roberts

[57] ABSTRACT

The invention relates to a process for the preparation of microcapsules having a capsule wall of polyurea and encapsulating a water-immiscible pesticide. The process comprises first dispersing a solution of a polyisocyanate in the sparingly water-soluble pesticide, in the presence of an anionic dispersant and at least one nonionic protective colloid and/or a nonionic surfactant, and subsequently reacting the dispersion with a polyamine, to give a stable aqueous suspension of microcapsules which can be used either direct or after dilution with water as pesticidal composition.

21 Claims, No Drawings

PROCESS FOR THE PREPARATION OF MICROCAPSULES

This application is a continuation of application Ser. No. 073,324, filed on Jul. 13, 1987, now abandoned, which is a continuation of application Ser. No. 776,080, filed Sept. 13, 1985, now abandoned.

The present invention relates to a process for the preparation of microcapsules having a capsule wall of polyurea and encapsulating a water-immiscible pesticide, by interfacial reaction of an aqueous dispersion of a solution of a polyisocyanate in the water-immiscible pesticide and an aqueous solution of a polyamine.

It is known per se to prepare microcapsules by interfacial reaction in a dispersion, with one of the reactive components required to form the capsule wall being dissolved in the disperse phase and the other being dissolved in the continuous phase. Such a process is disclosed for example in U.S. Pat. No. 3 577 515. This process is carried out by initially dispersing a solution of the first reactive component required to form the capsule wall in a continuous phase and then adding a solution of the second reactive component in the medium containing the continuous phase. In this process it is recommended to use nonionic protective colloids such as polyvinyl alcohol, gelatin and methyl cellulose for the dispersion of a water-immiscible organic phase in a continuous aqueous phase.

Another process of the above kind is disclosed in U.S. Pat. Nos. 4 280 833 and 4 417 916. In this process, a suspension of microcapsules with a capsule wall of polyurea is prepared, which microcapsules contain a herbicide. The process comprises dispersing a solution of polymethylenepolyphenylisocyanate in the herbicide in water and subsequently reacting the dispersion with an aqueous solution of a polyamine. The salient feature of this process resides in the use of salts of ligninsulfonic acid as dispersants.

An essential drawback of these known processes is that, when using the cited dispersants after addition of the second reactive component, a steep rise in viscosity occurs, which substantially lowers the stirrability of the mixture. This happens in particular when the concentration of the disperse phase consisting of active ingredient, isocyanate and optionally solvent is high, for example 50% or more. This reduction in stirrability adversely affects the reaction course, resulting in a delayed and incomplete reaction of the two components. The consequence is that the suspension of microcapsules obtained direct still contains unreacted polyamine in the aqueous phase and the capsules contain still unreacted polyisocyanate. This is undesirable, especially for the direct further use of the capsule suspension.

It is the object of the present invention to provide a process for the preparation of microcapsules having a capsule wall of polyurea, which process does not have the shortcomings of the known processes cited above and which makes it possible to prepare microcapsules in simple manner with complete reaction of the reactive components that form the capsule wall.

It has been found that this object of preparing microcapsules that encapsulate a pesticidal compound and have a capsule wall of polyurea can be attained by carrying out the reaction of the aqueous dispersion of a solution of a polyisocyanate in a pesticidal compound which is sparingly soluble in water with an aqueous solution of a polyamine, in the presence of a mixture of at least one anionic dispersant and a nonionic protective colloid and/or a nonionic surfactant.

Accordingly, the present invention relates to a process for the preparation of an aqueous suspension of microcapsules having a capsule wall of polyurea and encapsulating a water-immiscible pesticide, by dispersing a solution of a polyisocyanate in the sparingly water-soluble pesticide in water and subsequently reacting the dispersion with a polyamine, which process comprises effecting the dispersion of the solution of the polyisocyanate in the sparingly water-soluble pesticide in water and the subsequent reaction of the dispersion with the polyamine in the presence of an anionic dispersant and of at least one nonionic protective colloid and/or of a nonionic surfactant.

Suitable anionic dispersants are in general oligomers and polymers, as well as polycondensates, which contain a sufficient number of anionic groups to ensure their water-solubility. Examples of suitable anionic groups are sulfo groups or carboxyl groups; but polymers containing carboxyl groups can only be used in the higher pH range, preferably at a pH higher than 5. The number of anionic groups per polymer molecule is usually at least 60% of the number of monomer units contributing to the structure of the molecule. Oligomers and polymers that contain sulfo groups can be prepared either by polymerising monomers that contain sulfo groups or by sulfonating the appropriate oligomers or polymers. Polymers that contain carboxyl groups can be obtained by saponifying polyacrylates or polymethacrylates, in which case the degree of saponification must be at least 60%. Particularly suitable anionic dispersants are sulfonated polymers and condensates of aromatic sulfonic acids with formaldehyde. Typical examples of such anionic dispersants are:

A. Salts of polystyrenesulfonic acid, in particular the alkali metal, alkaline earth metal and ammonium salts, and the salts of organic amines which can be obtained by polymerising styrenesulfonic acid or salts thereof or by sulfonation of polystyrene and subsequent neutralisation with a suitable base, in which latter case the degree of sulfonation must be at least 60%;

B. Salts of polyvinylsulfonic acid, in particular the alkali metal, alkaline earth metal and ammonium salts, and the salts with organic amines which can be obtained by polymerising vinylsulfonic acid or salts thereof;

C. Salts of condensates of naphthalenesulfonic acids, preferably naphthalene-2-solfonic acid, with formaldehyde, in particular the alkali metal, alkaline earth metal and ammonium salts, and salts of thereof with organic amines which can be obtained by sulfonation of naphthalene, condensation of the resultant naphthalenesulfonic acids with formaldehyde, and neutralisation with a suitable base. The condensates may be represented by the formula

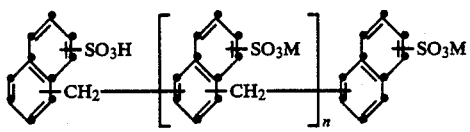

wherein M is sodium, potassium, magnesium, calcium, ammonium or the cation derived from an organic amine, and n is 1 to 25. The molecular weight of these compounds is in the range from about 500 to 6000.

D. Salts of condensates of naphthalenesulfonic acid with phenolsulfonic acid and formaldehyde, in particular the alkali metal, alkaline earth metal and ammonium salts, and salts with organic amines. These products are sulfo group containing polymers with an average molecular weight of 6000 to 8000, in which the momomer units naphthalene and phenol are linked to each other partly through methylene groups and partly through sulfo groups. Their approximate structure is:

also sulfonated. However, in this process, in particular when subsequently heating to 150°–170° C., large amounts of sulfones such as 4,4'-dihydroxydiphenylsulfone and 4-hydroxyphenylnaphthylsulfone are also formed in addition to phenolsulfonic acid. Hence a polymer whose monomer units naphthalene and phenol are linked partly through methylene groups and partly through sulfo groups is formed in the subsequent condensation with formaldehyde. In the preparation of

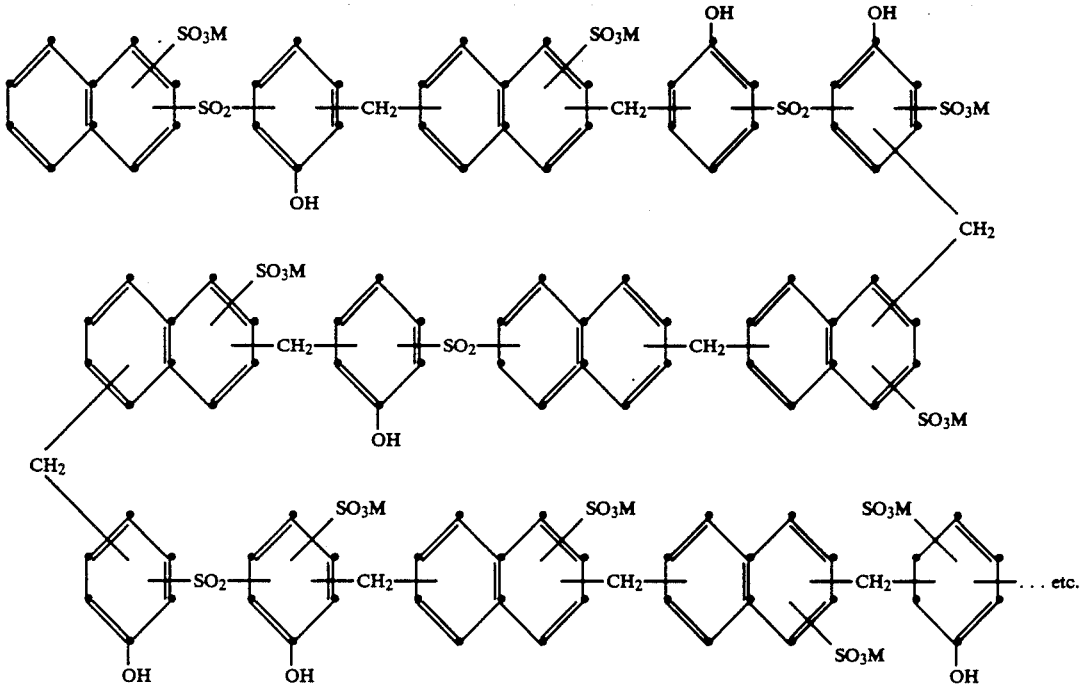

wherein M is sodium, potassium, magnesium, calcium, ammonium or the cation derived from an organic amine.

E. Salts of ligninsulfonic acid, in particular the sodium, potassium, magnesium, calcium or ammonium salt.

Preferred anionic dispersants are salts of polystyrenesulfonic acid (type A), salts of condensates of naphthalenesulfonic acid with formaldehyde (type C) and, in particular, condensates of naphthalenesulfonic acid with phenolsulfonic acid and formaldehyde (type D).

The condensates of naphthalenesulfonic acid with phenolsulfonic acid and formaldehyde of type D, which are especially preferred anionic dispersants, have so far not been described in the literature. They can be prepared by converting naphthalene, at 120°–130° C., first with concentrated sulfuric acid and/or oleum into naphthalenesulfonic acid, then adding phenol to the reaction mixture, and carrying out further reaction initially at 120°–130° C. and then removing the water of reaction in vacuo at 150°–170° C. and condensing the reaction product with formaldehyde after cooling to 90°–100° C., then neutralising the reaction mixture to pH 6–7 and evaporating it to dryness and granulating the residue, affording a water-soluble anionic dispersant (hereinafter referred to as "dispersant A") in granular form with an average molecular weight of 6000 to 8000.

The sulfonation of naphthalene under the above specified conditions yields mainly naphthalene-2-sulfonic acid together with insignificant amounts of naphthalenedisulfonic acid. Upon addition of phenol, this is dispersant A, naphthalene, phenol, sulfuric acid, formaldehyde and base may be used in the molar ratio of 1:0.5–1:2–2.5:0.4–0.8:2–3. The molar ratio of naphthalene:phenol:sulfuric acid:formaldehyde:base is conveniently 1:0.7:2:0.5:2, with sodium hydroxide being advantageously used as base. The sulfuric acid consists advantageously of mixtures of concentrated sulfuric acid and oleum, with the amount of free $SO_3$ in the oleum being at least equivalent to the amount of water in the concentrated sulfuric acid, so that at least 100% sulfuric acid is formed when mixing concentrated sulfuric acid and oleum. Formaldehyde is conveniently used as aqueous solution, for example as 37% aqueous solution. The separation of the water of reaction by distillation is advantageously effected under a pressure of 10–50 bar.

Suitable nonionic protective colloids are in general water-soluble polymers whose molecular weight is normally in the range from 10,000 to 200,000. The average diameter of the capsules can be influenced by the molecular weight of the respective polymer employed. The use of water-soluble polymers of low molecular weight results in a lower viscosity of the reaction mixture and thus in the formation of larger capsules, whereas the use of water-soluble polymers of high molecular weight leads to a higher viscosity of the reaction mixture and therefore to the formation of capsules of smaller diameter. Examples of suitable water-soluble polymers are: polyvinyl alcohol, polyvinyl methyl ether, polyvinylpyrrolidone, hydroxyethyl cellulose, hydroxypropyl cellulose, methyl cellulose (degree of substitution: 1.5-2), hydroxyethylmethyl cellulose, hydroxypropylmethyl cellulose, poly(2-hydroxyethyl)methacrylate, poly[2-(2-hydroxyethoxy)ethyl]methacrylate, polyethylene oxide (polyoxyethylene) and polyallyl alcohol (polyglycidol).

A preferred nonionic protective colloid is polyvinyl alcohol. Particularly preferred are polyvinyl alcohols with a viscosity of 4–60 cp (measured in 4% aqueous solutions at 20° C.), which have been prepared by saponification of polyvinyl acetate, with the degree of saponification being at least 60%, but preferably 80–95%. Suitable products of this kind are those commercially available under the registered trademark MOWIOL ®.

Suitable nonionic surfactants are in general nonionic water-soluble polymers having an average molecular weight of below 20,000, preferably below 5000. Particularly suitable nonionic surfactants of this kind are the products which can be obtained by reaction of ethylene oxide, or by the combined reaction of ethylene oxide and propylene oxide, with fatty alcohols, alkylphenols, fatty acids, fatty acid esters of polyhydroxy compounds, fatty acid amides and fatty amines, where the number of ethylene oxide and propylene oxide units may vary within wide limits. In general, the number of ethylene oxide units or ethylene oxide and propylene oxide units is from 1–200, preferably from 5–100 and, most preferably, from 8–40. Examples of suitable nonionic surfactants are:

alkylpolyethylene glycol ethers of the formula
$$R_1-O+CH_2-CH_2-O\!\!+\!\!_{n_1}\!\!H$$

wherein $R_1$ is $C_8$–$C_{20}$alkyl and $n_1$ is 2–100. Products of this kind are commercially available under the registered trademarks BRIJ ® (Atlas Chemical), ETHYLAN ® CD and ETHYLAN ® D (Diamond Shamrock), GENAPOL ® C, GENAPOL ® O and GENAPOL ® S (Hoechst AG);

alkylphenol polyethylene glycol ethers of the formula

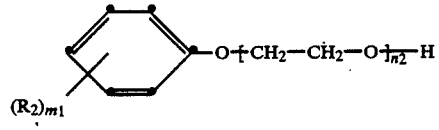

wherein $R_2$ is $C_8$–$C_{12}$alkyl, $m_1$ is 1 to 3 and $n_2$ is 2 to 40. Preferred meanings of $R_2$ are octyl and nonyl. Products of this kind are commercially available, for example under the registered trademarks Antarox (GAF), TRITON ® X (Röhm and Haas Co.), ATLOX ® 4991 (ICI), ARKOPAL ® N (American Hoechst) und ETHYLAN ® (Lankro Chem. Ltd);

α-phenethylphenol polyglycol ethers of the formula

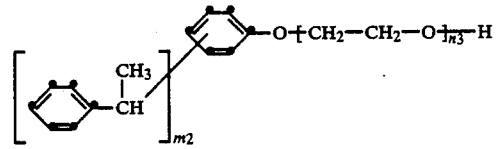

wherein $m_2$ is 1 to 3 and $n_3$ is 5 to 40. These products are designated ethoxylated styryl phenols. Commercially available products of this kind are for example: DISTY ® 125 (Geronazzo) and SOPROPHOR ® CY 18 (Rhone Poulenc S.A.);

fatty acid (polyethoxyethyl) esters of the formula

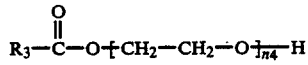

wherein $R_3$ is $C_8$–$C_{22}$alkyl or $C_{10}$–$C_{22}$alkenyl and $n_4$ is 2 to 50. These products are derived in particular from lauric acid, oleic acid and stearic acid. Such products are commercially available for example under the registered trademarks NONISOL ® (Ciba-Geigy) or MRYJ ® (ICI);

sorbitan polyethylene glycol ether fatty acid esters of the formula

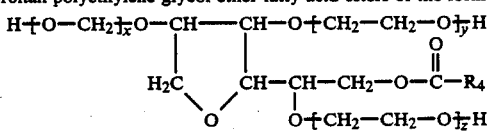

wherein $R_4$ is $C_8$–$C_{20}$alkyl and x, y and z are each 1 to 50, and the sum of $x+y+z$ is 20–150. Possible acid radicals $R_4$ are in particular the radicals of lauric acid, stearic acid, palmitic acid and oleic acid. Such products are also known as polysorbates and are commercially available for example under the registered trademark TWEEN ® (ICI);

triglyceride polyethylene glycol ethers of the formula

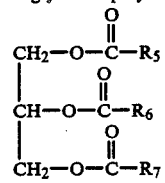

wherein $R_5$, $R_6$ and $R_7$ are the radical of the formula

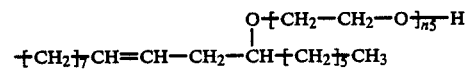

and each of $R_5$ and $R_6$ independently of the other is also $C_8$–$C_{20}$alkyl or $C_8$–$C_{20}$alkenyl, and $n_5$ is 3–100. Suitable acid radicals $R_5CO$— and $R_6CO$— containing $C_8$–$C_{20}$alkyl and $C_8$–$C_{20}$alkenyl groups are in particular the radicals of lauric acid, palmitic acid, stearic acid and oleic acid. A preferred representative of this type of surfactant is ethoxylated castor oil. Such products are commercially available under the registered trademark EMULSOGEN ® (Hoechst AG);

fatty acid polyethoxyethylamides of the formula

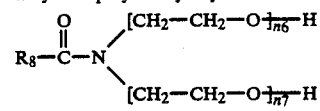

wherein $R_8$ is $C_8$–$C_{20}$alkyl, $C_8$–$C_{20}$alkenyl and $n_6$ and $n_7$ are each 1–25. Suitable acid radicals $R_8CO$— are in particular the radicals of lauric acid, oleic acid, palmitic acid and stearic acid. Products of this kind are commercially available for example under the registered trademarks AMIDOX® (Stephan Chemical Co.) and ETHOMID® (Armak Co.);

N-polyethoxyethylamines of the formula

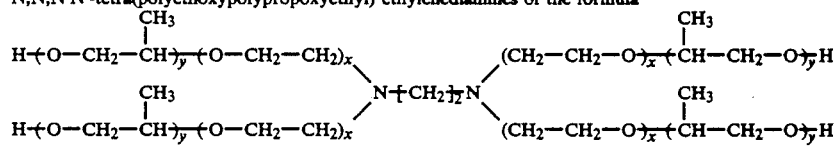

wherein $R_9$ is $C_8$-$C_{18}$alkyl or $C_8$-$C_{18}$alkenyl and $n_8$ is 1–15. The products derived from fatty amines, such as coconut fatty amine, oleylamine, stearylamine and tallow fatty amine, are particularly suitable. Such products are commercially available for example under the registered trademark GENAMIN® (Hoechst AG);

N,N,N'N'-tetra(polyethoxypolypropoxyethyl) ethylenediamines of the formula

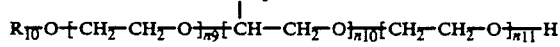

wherein x and y are each 2–50 and the sum of x+y is 4–100. Products of this kind are commercially available, especially under the registered trademarks TERRONIL® and TETRONIC® (BASF Wyandotte Corp.);

alkyl polyethylene glycol/polypropylene glycol ethers of the formula

wherein $R_{10}$ is hydrogen, $C_{8-20}$alkyl or $C_{8}$-$C_{20}$alkenyl and $n_9$ and $n_{11}$ are each 2–200, $n_{10}$ is 10–80 and the sum of $n_9+n_{10}+n_{11}$ is 15–450. Particularly suitable products of this kind are for example polyethylene oxide/polypropylene oxide block polymers ($R_{10}$=H) commercially available under the registered trademark PLURONIC® (BASF Wyandotte Corp.).

Preferred nonionic surfactants are ethylene oxide/propylene oxide block polymers (PLURONICS®), N,N,N',N'-tetra(polyethoxypolypropoxyethyl)ethylenediamines (TETRONICS®), nonylphenol polyglycol ethers containing 10–20 ethylene oxide units, alkyl polyethylene glycol ethers which are derived from fatty alcohols (GENAPOL®) and N-polyethoxyethylamines which are derived from fatty amines (GENAMIN®). Particularly preferred nonionic surfactants are ethylene oxide/propylene oxide block polymers (PLURONICS®).

Within the scope of this invention, polyisocyanates will be generally understood as meaning those compounds that contain two and more isocyanate groups in the molecule. Preferred isocyanates are di- and triisocyanates whose isocyanate groups may be linked to an aliphatic or aromatic moiety. Examples of suitable aliphatic diisocyanates are tetramethylene diisocyanate, pentamethylene diisocyanate and hexamethylene diisocyanate. Suitable aromatic isocyanates are toluylene diisocyanate (TDI: mixture of 2,4- and 2,6-isomers), diphenylmethane-4,4'-diisocyanate (MDI: DESMODUR® VL, Bayer), (polymethylene polyphenylisocyanate (MONDUR® MR, Mobay Chemical Company); PAPI®, PAPI® 135 (Upjohn Co.), 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4',4''-triphenylmethane triisocyanate. A further suitable diisocyanate is isophorone diisocyanate. Also suitable are adducts of diisocyanates with polyhydric alcohols such as ethylene glycol, glycerol and trimethylolpropane, obtained by addition, per mole of polyhydric alcohol, of a number of moles of diisocyanate corresponding to the number of hydroxyl groups of the respective alcohol. In this way several molecules of diisocyanate are linked through urethane groups to the polyhydric alcohol to form high molecular polyisocyanates. A particularly suitable product of this kind (DESMODUR® L) can be prepared by reacting 3 moles of toluylene diisocyanate with 1 mole of 2-ethylglycerol (1,1-bismethylolpropane). Further suitable products are obtained by addition of hexamethylene diisocyanate or isophorone diisocyanate with ethylene glycol or glycerol. Preferred polyisocyanates are diphenylmethane-4,4'-diisocyanate and polymethylene polyphenolisocyanate.

The di- and triisocyanates specified above can be employed individually or as mixtures of two or more such isocyanates.

Suitable polyamines within the scope of this invention will be understood as meaning in general those compounds that contain two and more amino groups in the molecule, which amino groups may be linked to aliphatic and aromatic moieties. Examples of suitable aliphatic polyamines are α,ω-diamines of the formula

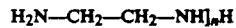

wherein n is an integer from 2–6. Exemplary of such diamines are ethylenediamine, propylene-1,3-diamine, tetramethylenediamine, pentamethylenediamine and hexamethylenediamine. A preferred diamine is hexamethylenediamine.

Further suitable aliphatic polyamines are polyethylenimines of the formula $H_2N-CH_2-CH_2-NH]_nH$ wherein n is an integer from 2 to 5. Representative examples of such polyethylenimines are: diethylenetriamine, triethylenetriamine, tetraethylenepentamine, pentaethylenehexamine.

Further suitable aliphatic polyamines are dioxaalkane-α,ω-diamines such as 4,9-dioxadodecane-1,12-diamine of formula

Examples of suitable aromatic polyamines are 1,3-phenylenediamine, 2,4-toluylenediamine, 4,4'-diaminodiphenylmethane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole and 1,4,5,8-tetraaminoanthraquinone. Those polyamines which are insoluble or insufficiently soluble in water may be used as hydrochlorides.

Yet further suitable polyamines are those that contain sulfo or carboxyl groups in addition to the amino groups. Examples of such polyamines are 1,4-phenylenediaminesulfonic acid, 4,4'-diaminodiphenyl-2-sulfonic acid, or diaminomonocarboxylic acids such as ornithine and lysine.

The above polyamines may be used individually or as mixtures of two or more polyamines.

Suitable pesticides that may be formulated in the process of this invention are those which
- are insoluble in but stable to water,
- are liquid at room temperature or have a melting point $\leq 60°$ C., or those that are soluble in a water-immiscible organic solvent,
- are inert to isocyanates, and
- are able to dissolve polyisocyanates of the above specified kind.

Suitable water-immiscible solvents in which the pesticides may be dissolved are aliphatic and aromatic hydrocarbons such as hexane, cyclohexane, benzene, toluene, xylene, mineral oil or kerosin. Also suitable are cyclohexanone, as well as halogenated hydrocarbons such as methylene chloride, chloroform and o-dichlorobenzene. The mixtures of mono- and polyalkylated aromatics commercially available under the registered trademark SHELLSOL ® are also suitable.

In the process of this invention, it is possible to formulate a very wide range of pesticides, for example herbicides, plant growth regulators, insecticides, acaricides, nematicides, safeners and ectoparasiticides. With respect to their chemical constitution, these pesticides may belong to a very wide range of compound classes. Examples of compound classes to which the pesticides which can be formulated in the process of this invention may belong are: dinitroanilines, acylalanines, triazole derivatives, carbamates, phosphoric acid esters, pyrethroids, benzilic acid esters, polycyclic halogenated hydrocarbons, formamidines and dihydro-1,3-thiazol-2-ylidene anilines. Examples of suitable individual compounds of the above mentioned compound classes are listed hereinafter. Where known, the common name is used to designate the individual compounds (q.v. the Pesticide Manual, 7th edition, 1983, British Crop Protection Council).

s-Triazines

Atrazin, Propazin, Terbutylazin; Ametryn, Azipro-tryn, Desmetryn, Dipropetryn, Prometryn, Terbutryn; Secbumeton, Terbumeton.

Ureas

Chlorobromuron, Chloroxuron, Chlorotoluron, Fluometuron, Metobromuron, Thiazafluron.

Haloacetanilides

Dimethachlor, Metolachlor, Pretilachlor, 2-chloro-N-(1-methyl-2-methoxyethyl)-acet-2,6-xylidide, Alachlor, Butachlor, Diethatyl ethyl, Propachlor.

Diphenyl ether derivates

Bifenox, Diclofopmethyl, 4-(4-Pentyn-1-yloxy) diphenyl ether.

Phenoxypropionic acid derivatives

Fluazifop.

Dinitroanilines

Butralin, Ethalfluralin, Fluchloralin, Isopropalin, Pendimethalin, Profluralin, Trifluralin.

Acylalanines

Fluralaxyl, Metalaxyl; Benzoylprop ethyl, Flamprop methyl.

Triazole derivates

Etaconazol, Propiconazol, 1-[2-(2,4-dichlorophenyl)-pent-1-yl]-1H-1,2,4-triazole; Triadimefon.

Carbamates

Dioxacarb, Furathiocarb; Aldicarb, Benomyl, 2-sec-butylphenylmethylcarbamate, Etiofencarb, Isoprocarb, Propoxur; Carbetamid, Butylat, Di-allat, EPTC, Molinat, Thiobencarb, Triallat, Vernolat.

Phosphoric acid esters

Piperophos, Anilofos, Butamifos; Azamethiphos, Chlorfenvinphos, Dichlorvos, Diazinon, Methidathion; Azinphos ethyl, Azinphos methyl, Chlorpyrifos, Chlorthiofos, Crotoxyphos, Cyanophos, Demeton, Dialifos, Dimethoate, Disulfoton, Etrimfos, Famphur, Flusulfothion, Fluthion, Fonofos, Formothion, Heptenophos, Isofenphos, Isoxathion, Malathion, Mephospholan, Mevinphos, Naled, Oxydemeton methyl, Oxydeprofos, Parathion, Phoxim, Pyrimiphos methyl, Profenofos, Propaphos, Propetamphos, Prothiophos, Quinalphos, Sulprofos, Phemephos, Terbufos, Triazophos, Trichloronate; Fenamipos, Isazophos; s-benzyl-o,o-diisopropylphosphorothioate, Edinphos, Pyrazophos;

Pyrethroids

Allethrin, Bioallethrin, Bioresmethrin, Cyhalotrin, Cypermethrin, Deltamethrin, Fenpropathrin, Fenvalerate, Flucythrinate, Fluvalinate, Permethrin, Pyrethrine, Resmethrin, Tetramethrin, Tralomethrin.

Benzilic acid esters

Brompropylat, Chlorbenzylat, Chlorpropylat.

Polycyclic halogenated hydrocarbons

Aldrin, Endosulfan.

Formamidines

Chlordimeform.

Dihydro-1,3-thiazol-2-ylidene-anilines

N-(2,3-Dihydro-3-methyl-1,3-thiazol-2-ylidene)-2,4-xilidine.

Miscellaneous

Methopren, Kinopren; Flupropimorph, Tridemorph; Bromoxynil; Crimidine, Bupyrimate; Sethoxydim; Chlorphenprop-methyl; Carboxin; Buthiobate, Amithraz; Dicofol; Oxadiazon; Prochloraz; Propargite; Dicamba; Camphechlor; Chlorfenson.

The microcapsules which can be prepared by the process of this invention may contain the above specified pesticides individually or as combinations of two or more pesticides.

The process of this invention for the preparation of microcapsules is conveniently carried out by first dissolving the anionic dispersant and the nonionic protective colloid and/or nonionic surfactant in water and then adding a solution of one or more polyisocyanates of the aforementioned kind in one or more of the above specified pesticides or in a solution of one or more of these pesticidal compounds in a water-immiscible organic solvent, and stirring the mixture efficiently until a homogeneous dispersion is obtained. With continued stirring, one or more polyamines of the above indicated kind is added and the mixture is further stirred until the polyamine has fully reacted with the isocyanate. The polyamines are conveniently added as aqueous solution.

The process of this invention can be carried out at room temperature or at moderately elevated temperature. A suitable temperature range is from 10°–75° C. It is preferred to carry out the process of this invention in the temperature range from 20°–45° C.

The reaction time for the reaction of the polyisocyanate with the polyamine is normally from 2 to 30 minutes. The degree of conversion and the end of the reaction can be determined by titration of the free amine present in the aqueous phase.

The components required to form the capsule walls may generally be employed in an amount of 2.5 to 30% by weight, preferably 5 to 20% by weight, based on the material to be encapsulated. The material to be encapsulated may consist of one active ingredient or of a mixture of two and more active ingredients, or of a solution of an active ingredient or of a mixture of two and more active ingredients in a water-immiscible solvent. The amount of components required to form the capsule wall in each specific case depends primarily on the wall thickness of the capsules to be prepared and also on the capsule size.

In the process of this invention it is possible to prepare aqueous suspensions of microcapsules that contain 100–700 g of microcapsules per liter. The suspensions obtainable in the process of this invention preferably contain 400–600 g of microcapsules per liter.

The suspensions of microcapsules obtainable in the process of this invention are directly ready for use. However, for transportation and storage they can be stabilised by the addition of further ingredients such as surface-active agents, thickeners, antifoams and antifreeze agents.

It is, however, also possible to separate the microcapsules from the directly obtained suspension by filtration or centrifugation and either to dry or convert them once more into a suspension. The microcapsules which have been isolated from the suspension and dried are in the form of a flowable powder that has a virtually unlimited shelf life.

Even when dispersing the solution of the polyisocyanate in the pesticide, the simultaneous use in the process of this invention of an anionic dispersant and a nonionic protective colloid and/or nonionic surfactant prevents the sharp rise in viscosity that occurs particularly if an anionic dispersant alone is used, for example a lignosulfonate. It is thus not only easier to carry out the process, but also simultaneously to achieve a more rapid and more complete reaction of polyisocyanate and polyamine, thereby substantially preventing the formation of undesirable by-products. Lowering the viscosity of the reaction mixture also leads to the formation of a finer dispersion at the same shearing force and thus to a reduction in the diameter of the capsules obtained. The capsule suspensions prepared by the process of this invention are stable and, even on prolonged storage, exhibit no formation of serum or sediment. Further, by appropriate choice of the kind and amount of the anionic and nonionic dispersants, the capsule suspensions obtainable in the process of this invention exhibit thixotropic properties and can therefore be brought in simple manner into a readily flowable state by shaking or stirring.

In the following Examples, which illustrate the invention in more detail, the registered trademarks and other designations that are not self-evident denote the following products:

Anionic dispersants

Dispersant A: sodium salt of a condensate of naphthalenesulfonic acid with phenolsulfonic acid and formaldehyde, prepared according to Example 1.

TAMOL ® SN: sodium salt of a condensate of naphthalenesulfonic acid and formaldehyde, supplier Rohm & Haas Co.

Nonionic dispersants (protective colloids)

MOWIOL ® 18–88: polyvinyl alcohol with a viscosity of 18 cp (measured in a 4% aqueous solution at 20° C.), prepared by saponification of polyvinyl acetate (degree of saponification: 88%), supplier Hoechst AG.

MOWIOL ® 40–88: polyvinyl alcohol with a viscosity of 40 cp (measured in a 4% aqueous solution at 20° C.), prepared by saponification of polyvinyl acetate (degree of saponification: 88%), supplier Hoechst AG.

Nonionic surfactants

PLURONIC ® F-108: ethylene oxide/propylene oxide block polymer of the formula $(EO)_x$—$(PO)_y$—$(EO)_z$, with mol wt of c. 16,000 and an ethylene oxide content of 80%, supplier BASF Wyandotte Corp.

PLURONIC ® P-85: ethylene oxide/propylene oxide polymer of the formula $(EO)_x$—$(PO)_y$—$(EO)_z$, with mol wt 4500 and an ethylene oxide content of 50%, supplier BASF Wyandotte Corp.

PLURONIC ® L-42: ethylene oxide/propylene oxide block polymer of the formula $(EO)_x$—$(PO)_y$—$(EO)_z$, with mol wt 1450 and an ethylene oxide content of 20%, supplier BASF Wyandotte Corp.

TETRONIC ® 707: ethoxylated/propoxylated ethylenediamine with mol wt 12000 and an ethylene oxide content of 70%, supplier BASF Wyandotte Corp.

ANTAROX ® CO 710: nonylphenol polyglycol ether containing 10 ethylene oxide units, supplier GAF.

GENAPOL ® C-200: ethoxylated coconut fatty alcohol containing 25 ethylene oxide units, supplier Hoechst AG.

GENAMIN ® T100: ethoxylated tallow fatty amine containing 10 ethylene oxide units, supplier Hoechst AG.

Solvent

SHELLSOL ® AB: mixture of mono- and polyalkylated aromatic hydrocarbons, supplier Shell.

EXAMPLE 1

Preparation of dispersant A

Starting materials:
288 g (2.25 moles) of naphthalene 144 g (1.53 moles) of phenol
440 g (4.48 moles) of 100% sulfuric acid
78.5 g (0.97 mole) of 37% aqueous formaldehyde solution
370 g (4.4 moles) of 48% aqueous sodium hydroxide solution The naphthalene is melted in a stirred reactor and, after addition of sulfuric acid, the melt is heated for 4 hours to 120°–125° C. The phenol is then added and the temperature is kept for a further hour at 120°–125° C. The reaction vessel is subsequently evacuated to a pressure of 15 bar and the temperature is increased slowly to 160° C. and kept for 3 hours while distilling off the water of reaction. The reaction mixture is cooled to 105°–110° C. and homogenised by stirring. The batch is then cooled to 90° C. by cautiously adding 200 g of ice, while maintaining the homogeneity of the mixture by continual stirring. The formaldehyde solution is then added at 90°–95° C. over 1 hour and stirred for 3 hours at 95° C. A sample of the reaction mixture then forms with water a clear 5% solution and no longer smells of formaldehyde. The reaction mixture is then cooled to 80° C. by addition of 60 g of ice and 60 g of water. After addition of a further 180 ml of water, the reaction mixture is neutralised with about 230–250 ml of 48% sodium hydroxide solution at a temperature of 80° C. The pH of a 10% solution of a sample of the reaction mixture is about 6.5. The reaction mixture is then evaporated to dryness and the residue is granulated, affording 900 g of dispersant A in the form of water-soluble granules.

EXAMPLE 2

In a 2 liter glass beaker, a solution of 360 g of N-chloroacetyl-N-(1-methyl-2-methoxyethyl)-2,6-dimethylaniline and 70.8 g of diphenylmethane-4,4'-diisocyanate in 353 g of SHELLSOL® AB is dispersed at 27°–33° C. with an impeller in a solution of 15 g of dispersant A and 15 g of MOWIOL® 18-88 (in the form of a 10% aqueous solution) in 360 g of water. After about 1 minute, 30.8 g of hexamethylenediamine (in the form of a 40% aqueous solution) are added with further stirring, the temperature rising to about 40° C. Upon addition of the hexamethylenediamine, stirring is continued slowly for 1 hour, during which time the reaction mixture cools to room temperature. The suspension is stabilised by addition of 15 g of PLURONIC® F-108, affording a low viscosity suspension of microcapsules with capsule diameters of 2–20 μm.

EXAMPLE 3

Using an impeller, a solution of 37.3 g of diphenylmethane-4,4'-diisocyanate in 480 g of Metolachlor is dispersed in a solution of 7.5 g of dispersant A and 7.5 g of MOWIOL® 40-88 (in the form of a 10% aqueous solution) in 232.5 g of water, the temperature rising by 3°–5° C. With further stirring, 16.4 g of hexamethylenediamine (in the form of a 40% aqueous solution) are added, the temperature rising by a further 8°–12° C. After addition of hexamethylenediamine, stirring is continued for 1 hour and the suspension, which has cooled to room temperature, is stabilised with PLURONIC® F-108, affording a low viscosity storage-stable capsule suspension with a capsule size of 2–30 μm.

EXAMPLE 4

In a 2 liter glass beaker, a solution of 87 g of diphenylmethane-4,4'-diisocyanate in 1080 g of diazinone is dispersed with an impeller in a solution of 9.0 g of dispersant A and 9.0 g of MOWIOL® 18-88 (in the form of a 10% aqueous solution) in 392 g of water. After about 1 minute, 38 g of hexamethylenediamine (in the form of a 40% aqueous solution) is added, the temperature rising by 5°–8° C. Stirring is continued for 1 hour and the resultant capsule suspension is stabilised by addition of a solution of 29 g of GENAMIN® T 100 in 80 g of water, affording a stable capsule suspension with a viscosity of 700–1200 cp and an average particle size of 2–5 μm.

The ratio of dispersant to MOWIOL® 18-88 can be varied in the range from 3:1 to 1:3, the quality of the suspension of microcapsules remaining virtually the same.

EXAMPLE 5

Using an impeller, a solution of 8.1 g of diphenylmethane-4,4'-diisocyanate in 100 g of Furathiocarb is dispersed at 50° C. in a solution of 1.5 g of dispersant A and 1.5 g of MOWIOL® 18-88 (in the form of a 10% aqueous solution) in 55 g of water. With further stirring, 3.5 g of hexamethylenediamine (in the form of a 40% aqueous solution) are added to the dispersion, the temperature of the mixture rising by about 3° C. After addition of the hexamethylenediamine, the resultant suspension is further stirred for 1 hour, during which time the suspension of microcapsules cools to room temperature. Then 10 g of GENAMIN® T 100 are added, affording a low viscosity storage-stable suspension of microcapsules with an average capsule size of 2–50 μm.

EXAMPLE 6

In a glass beaker, a solution of 6.3 g of diphenylmethane-4,4'-diisocyanate and 24 g of N-(2,3-dihydro-3-methyl-1,3-thiazol-2-ylidene)-3,4-xylidene in 47.2 g of SHELLSOL® AB is dispersed at room temperature with an impeller in a solution of 0.83 g of dispersant A and 0.83 g of MOWIOL® 40-88 (in the form of a 10% aqueous solution) in 58 g of water. Then 6 g of hexamethylenediamine (in the form of a 40% aqueous solution) are added, the temperature rising by about 2° C. Upon addition of the hexamethylenediamine the mixture is stirred for 1 hour, in the course of which time the resultant capsule suspension cools to room temperature. The readily flowable capsule suspension so obtained has a viscosity of 150–300 cp and the average capsule size is 5–20 μm.

EXAMPLE 7

In a glass beaker, a solution of 8.5 g of diphenylmethane-4,4'-diisocyanate in 100 g of Profenofos is dispersed at room temperature with an impeller in a solution of 1 g of dispersant A and 1 g of MOWIOL® 18-88 in 70 g of water. With further stirring, 3.7 g of hexamethylenediamine (in the form of a 40% aqueous solution) are added and the mixture is further stirred, affording a stable suspension of microcapsules with good suspension power and a viscosity of about 100 cp. The average capsule size is about 5–15 μm.

EXAMPLE 8

A solution of 19.7 g of diphenylmethane-4,4'-diisocyanate in 80 g of Isazofos is dispersed at room temperature with an impeller in a solution of 8 g of dispersant A and 0.8 g of MOWIOL® 18-88 in 44.2 g of water. Then 8.6 g of hexamethylenediamine (in the form of a 40% aqueous solution) are added to the resultant dispersion, the temperature rising by about 10° C. The mixture is further stirred for 30 minutes at room temperature, affording a stable suspension of microcapsules containing 35% by weight of polyurea, based on the amount of active ingredient employed.

EXAMPLE 9

With efficient stirring, a mixture of 8.1 g of diphenylmethane-4,4'-diisocyanate, 80 g of Propiconazol and 15.4 g of xylene is dispersed at room temperature in a solution of 1.6 g of dispersant A, 0.8 g of MOWIOL ® 18–88 and 0.8 g of PLURONIC ® F 108 in 58.6 g of water. Then 3.3 g of hexamethylenediamine (in the form of a 40% aqueous solution) are added and stirring is continued for 1 hour, affording a low viscosity stable aqueous suspension of microcapsules with an average capsule diameter of 2–3 μm. The suspension has an active ingredient content of 46% by weight.

EXAMPLE 10

With efficient stirring, a solution of 42.5 g of xylene and 44.5 g of diphenylmethane-4,4'-diisocyanate in 480 g of Propiconazol is dispersed at room temperature in a solution of 20 g of dispersant A and 8 g of PLURONIC ® F 108 in 247.6 g of water. Then 18.4 g of hexamethylenediamine (in the form of a 40% aqueous solution) are added, the temperature rising by about 10° C. The mixture is further stirred until it has cooled to room temperature. The stable low viscosity suspension of microcapsules so obtained has an average capsule size of 3–5 μm and an active ingredient content of 54% by weight.

EXAMPLE 11

With efficient stirring, a solution of 75.4 g of diphenylmethane-4,4'-diisocyanate in 463.7 g of Metalochlor is dispersed in a solution of 15 g of sodium polystyrenesulfonate and 10 g of PLURONIC ® F 108 in 328 g of water. Then 32.8 g of hexamethylenediamine (in the form of a 10% aqueous solution) are added, the temperature rising by about 15° C. The mixture is further stirred until it has cooled to room temperature, affording a suspension of microcapsules with an average capsule size of 1–2 μm.

EXAMPLE 12

With efficient stirring, a solution of diphenylmethane-4,4'-diisocyanate in 100 g of Metalochlor is dispersed at room temperature in a solution of 1.5 g of sodium polystyrenesulfonate and 1.5 g of MOWIOL ® 40–88 in 76.6 g of water. Then 3.5 g of hexamethylenediamine (in the form of a 40% aqueous solution) are added, the temperature rising by about 10° C. The mixture is further stirred for 1 hour, affording a stable suspension of microcapsules with an average capsule size of 1–2 μm.

EXAMPLE 13

With efficient stirring, a solution of 6.5 g of diphenylmethane-4,4'-diisocyanate in 80 g of Metalochlor is dispersed at room temperature in a solution of 1.6 g of dispersant A and 1.6 g of GENAPOL ® C-200 in 61 g of water. Then 2.7 g of hexamethylenediamine (in the form of a 40% aqueous solution) are added, the temperature rising by about 7° C. The mixture is further stirred until it has cooled to room temperature, affording a suspension of microcapsules with a viscosity of 150 cp and an average capsule size of 5–6 μm. The capsule suspension disperses spontaneously when diluted with water.

EXAMPLE 14

The procedure of Example 13 is repeated, using ANTAROX ® CO 710 instead of GENAPOL ® C-200. The temperature rises by 6° C. upon addition of hexamethylenediamine. The suspension of microcapsules so obtained has a viscosity of 880 cp and an average capsule size of 5 μm, and disperses spontaneously when diluted with water.

EXAMPLE 15

The procedure of Example 13 is repeated, using an ethoxylated dinonylphenol with 150 ethylene oxide units instead of GENAPOL ® C-200. The temperature rises by 5° C. upon addition of hexamethylenediamine. The suspension of microcapsules so obtained has a viscosity of 65 cp and an average capsule size of 4 μm, and disperses spontaneously when diluted with water.

EXAMPLE 16

The procedure of Example 13 is repeated, using PLURONIC ® P-85 instead of GENAPOL ® C-200, affording a suspension of microcapsules with a viscosity of 30 cp and an average capsule size of 4 μm, and which disperses spontaneously when diluted with water.

EXAMPLE 17

The procedure of Example 13 is repeated, using PLURONIC ® L-42 instead of GENAPOL ® C-200. The resultant suspension of microcapsules is initially of low viscosity, but thickens over 24 hours to a viscosity of 1600 cp. The suspension can be readily shaken. The average capsule size is 3.5–4 μm.

EXAMPLE 18

The procedure of Example 13 is repeated, using TETRONIC ® 707 instead of GENAPOL ® C-200. The temperature rises by 5° C. upon addition of hexamethylenediamine. The resultant suspension of microcapsules has a viscosity of 500 cp and an average capsule size of 5 μm, and disperses spontaneously when diluted with water.

EXAMPLE 19

With efficient stirring, a solution of 75.4 g of diphenylmethane-4,4'-diisocyanate in 463.7 g of Metalochlor is dispersed at room temperature in a solution of 15 g of dispersant A and 10 g of PLURONIC ® F 108 in 360 g of water. Then 32.8 g of hexamethylenediamine (in the form of a 40% aqueous solution) are added, the temperature rising by about 15° C. The mixture is further stirred until it has cooled to room temperature, affording a suspension of microcapsules with a viscosity of 60 cp and an average capsule diameter of 2 μm.

EXAMPLE 20

A solution of 35.5 g of polymethylene polyphenylisocyanate [MONDUR ® MR (Mobay Chemical Company)] in 465 g of Metalochlor is dispersed at room temperature in a 1.5 liter glass beaker with an impeller in a solution of 20 g of TAMOL ® SN, 10 g of PLURONIC ® F 108 and 50 g of ethylene glycol in 348.5 g of water. The mixture is stirred for 2 minutes, the temperature rising by 3°–15° C. Then 15.5 g of hexamethylenediamine (in the form of a 40% aqueous dispersion) are added to the dispersion and the temperature rises by a further 7°–12° C. The resultant suspension of microcapsules is stirred for a further hour and then adjusted to pH 7 with hydrochloric acid. After addition of 19.5 g of a 3.6% dispersion of xantham (polysaccharide), a storage stable suspension of microcapsules with a viscosity of 200–500 cp is obtained. Depending on the rate of stirring, the capsule diameter is 4–30 μm.

EXAMPLE 21

A solution of 39 g of polymethylene polyphenylisocyanate (PAPI ® 135) in 511 g of Isazophos is dispersed at room temperature in a 1.5 liter glass beaker with an impeller in a solution of 22 g of TAMOL ® SN, 11 g of PLURONIC ® F 108 and 55 g of ethylene glycol in 372.4 g of water. The dispersion is stirred for 2 minutes, the temperature rising by 10°–15° C. Then 15.5 g of hexamethylenediamine (in the form of a 40% aqueous solution) are added, the temperature rising by a further 7°–12° C. Stirring is continued for a further hour and the reaction mixture is neutralized to pH 7 with hydrochloric acid. Then 19.5 g of a 3.6% dispersion of xantham (polysaccharide) in water are added, affording a storage stable suspension of microcapsules with a viscosity of 200–500 cp. Depending on the rate of stirring, the capsule diameter is 2–8 μm.

EXAMPLE 22

With efficient stirring, a solution of 20.4 g of dichloromethane and 7.5 g of diphenylmethane-4,4'-diisocyanate in 80 g of N-chloroacetyl-N-(1-methyl-2-methoxyethyl)-2,6-dimethylaniline is dispersed at room temperature in a solution of 1.8 g of dispersant A and 1.8 g of PLURONIC ® F 108 in 66.9 g of water. Then 3.1 g of hexamethylenediamine (in the form of a 40% aqueous solution) are added, the temperature rising by about 10° C. The resultant stable low viscosity suspension of microcapsules has an average capsule size of 2–4 μm and an active ingredient content of 43% by weight.

EXAMPLE 23

With efficient stirring, a solution of 18 g of diphenylmethane-4'4-diisocyanate in 96 g of Chlorofenvinphos is dispersed at room temperature in a solution of 1.6 g of dispersant A and 1.6 g of PLURONIC ® F 108 in 50.5 g of water. Then 7.4 g of hexamethylenediamine (in the form of a 40% aqueous solution) are added, the temperature rising by 20°–30° C. The mixture is further stirred until it has cooled to room temperature. The resultant stable low viscosity suspension of microcapsules (viscosity=150 cp) with an average capsule size of 2–3 μm has an active ingredient content of 51.5% by weight and a capsule wall content of 13.6% by weight.

EXAMPLE 24

With efficient stirring, a solution of 87 g of diphenylmethane-4,4'-diisocyanate in 1080 g of diazinone is dispersed at room temperature in a solution of 9.0 g of dispersant A, 3.0 g of MOWIOL ® 18-88 (in the form of a 10% aqueous solution) and 6.0 g of PLURONIC ® F 108 in 446 g of water. Then 37.9 g of hexamethylenediamine (in the form of a 40% aqueous solution) are added, the temperature rising by 3°–5° C. The resultant liquid suspension of microcapsules with an average capsule size of 1.5–2.5 μm has a viscosity of 250–600 cp. It contains 61.6% by weight of active ingredient and has a capsule wall content of 7.1% by weight.

What is claimed is:

1. In a process for the preparation of an aqueous suspension of microcapsules having a capsule wall of polyurea and encapsulating a water-immiscible pesticide, by dispersing a solution of a polyisocyanate in the sparingly water-soluble pesticide in water and subsequently reacting the dispersion with a polyamine, the improvement which comprises effecting the dispersion of the solution of the polyisocyanate in the sparingly water soluble pesticide in water and the subsequent reaction of the dispersion with the polyamine in the presence of an effective viscosity-reducing amount of (a) an anionic dispersant selected from the group consisting of a salt of polystyrenesulfonic acid, a salt of polyvinylsulfonic acid, a salt of a condensate of naphthalenesulfonic acid and formaldehyde, a salt of a condensate of naphthalenesulfonic acid with phenolsulfonic acid and formaldehyde, and a salt of ligninsulfonic acid, and (b) at least one nonionic protective colloid or nonionic surfactant or both.

2. A process according to claim 1, which comprises the use of an anionic dispersant which is a salt of polystyrenesulfonic acid, a salt of a condensate of naphthalenesulfonic acid with formaldehyde or a salt of a condensate of naphthalenesulfonic acid with phenolsulfonic acid and formaldehyde.

3. A process according to claim 1, which comprises the use of an anionic dispersant which is a salt of a condensate of naphthalenesulfonic acid with phenolsulfonic acid and formaldehyde.

4. A process according to claim 1, which comprises the use of a nonionic protective colloid which is a water-soluble polymer with a molecular weight of 10,000 to 200,000.

5. A process according to claim 3, which comprises the use of a nonionic protective colloid which is a polymer selected from the group consisting of polyvinyl alcohol, polyvinyl methyl ether, polyvinylpyrrolidone, hydroxyethyl cellulose, hydroxypropyl cellulose, methyl cellulose, hydroxyethyl cellulose, hydroxypropylmethyl cellulose, poly(2-hydroxyethyl)methacrylate, poly[2-(2-hydroxyethoxy)ethyl)methacrylate, polyethylene oxide and polyallyl alcohol.

6. A process according to claim 4, wherein polyvinyl alcohol is used as nonionic protective colloid.

7. A process according to claim 5, which comprises the use of a nonionic protective colloid which is a polyvinyl alcohol with a viscosity of 4–60 cp (measured in 4% aqueous solutions at 20° C.) and which has been prepared by saponifying polyvinyl acetate to a degree of saponification of 80–95%.

8. A process of claim 1, which comprises the use of a nonionic surfactant which is an ethylene oxide/propylene oxide block polymer or is a product obtained by reaction of ethylene oxide, or by combined reaction of ethylene oxide and propylene oxide, with a substance selected from the group consisting of fatty alcohols, alkylphenols, fatty acids, fatty acid esters of polyhydroxy compounds, fatty acid amides and fatty amines.

9. A process according to claim 8, which comprises the use of a nonionic surfactant which is an ethylene oxide/propylene oxide block polymer, a N,N,N',N'-tetra(polyethoxypolypropoxyethyl)ethylenediamine, a nonylphenol polyglycol ether, an ethoxylated fatty alcohol or an ethoxylated fatty amine.

10. A process according to claim 8, which comprises the use of a nonionic surfactant which is an ethylene oxide/propylene oxide block polymer.

11. A process according to claim 1, which comprises using a polyisocyanate selected from the group consisting of tetramethylene diisocyanate, pentamethylene diisocyanate, hexamethylene diisocyanate, toluylene diisocyanate, diphenylmethane-4,4'-diisocyanate, polymethylene polyphenylisocyanate, 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate, 4,4',4''-triphenylmethane triisocyanate and isophorone diisocyante.

12. A process according to claim 11, which comprises using diphenylmethane-4,4'-diisocyanate or polymethylenepolyphenylisocyanate.

13. A process according to claim 1, which comprises using a polyamine selected from the group consisting of ethylenediamine, propylene-1,3-diamine, tetramethylenediamine, pentamethylenediamine, hexamethylenediamine, diethylenetriamine, triethylenetetramine, tetraethylenepentamine, pentaethylenehexamine, 4,9-dioxadodecane-1,12-diamine, 1,3-phenylenediamine, 2,4-toluylenediamine, 4,4'-diaminodiphenylmethane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole, and 1,4,5,8-tetraaminoanthraquinone.

14. A process according to claim 13, wherein hexamethylenediamine is used.

15. A process according to claim 1, which comprises using a pesticide selected from the group consisting of haloacetanilides, triazole derivatives, carbamates, phosphoric acid esters, and dihydro-1,3-thiazol-2-ylidine anilines.

16. A process according to claim 1, wherein the process is carried out in the temperature range from 10°-75° C.

17. A process according to claim 16, wherein the process is carried out in the temperature range from 20°-45° C.

18. A process according to claim 1, wherein the components required to form the capsule walls are employed in an amount of 2.5 to 30% by weight, based on the material to be encapsulated.

19. A process according to claim 18, wherein the components required to form the capsule walls are employed in an amount of 5 to 20%, based on the material to be encapsulated.

20. A process according to claim 1, which comprises using in addition to the amounts of anionic dispersant and nonionic protective colloid and/or nonionic surfactant an amount of water sufficient to form a suspension of microcapsules which contains 100 to 700 g of microcapsules per liter.

21. A process according to claim 20, which comprises using in addition to the amounts of anionic dispersant and nonionic protective colloid and/or nonionic surfactant an amount of water sufficient to form a suspension of microcapsules which contains 400 to 600 g of microcapsules per liter.

* * * * *